(12) United States Patent
Landsman et al.

(10) Patent No.: US 8,490,307 B2
(45) Date of Patent: Jul. 23, 2013

(54) PATIENT IDENTIFICATION SYSTEMS AND METHODS OF USE, INCLUDING RECIPIENT VERIFICATION

(75) Inventors: Kelly M. Landsman, Milwaukee, WI (US); Luke A. Westra, Chicago, IL (US)

(73) Assignee: Typenex Medical, LLC, Chicago, IL (US)

( * ) Notice: Subject to any disclaimer, the term of this patent is extended or adjusted under 35 U.S.C. 154(b) by 70 days.

(21) Appl. No.: 12/853,292

(22) Filed: Aug. 10, 2010

(65) Prior Publication Data

US 2012/0036753 A1 Feb. 16, 2012

Related U.S. Application Data

(60) Provisional application No. 61/232,220, filed on Aug. 7, 2009.

(51) Int. Cl.
*A44C 5/00* (2006.01)
*A61B 5/103* (2006.01)
*A61B 5/117* (2006.01)
*G09F 3/14* (2006.01)

(52) U.S. Cl.
USPC .............................. 40/633; 40/665; 40/654.01

(58) Field of Classification Search
USPC ........................ 40/633, 665, 654.01
See application file for complete search history.

(56) References Cited

U.S. PATENT DOCUMENTS

| | | | |
|---|---|---|---|
| 2,871,592 A | 2/1959 | Polzin | |
| 2,893,143 A | 7/1959 | Mosher, Jr. et al. | |
| 2,911,743 A | 11/1959 | Pokras | |
| 3,020,657 A | 2/1962 | Clark | |
| 3,197,899 A | * | 8/1965 | Twentier .................... 40/633 |
| 3,279,107 A | 10/1966 | Baumgartner | |
| 3,751,835 A | 8/1973 | Smith | |

(Continued)

FOREIGN PATENT DOCUMENTS

| CA | 1 272 021 | | 7/1990 | |
|---|---|---|---|---|
| CA | 1272021 A | * | 7/1990 | .................... 40/665 |

(Continued)

OTHER PUBLICATIONS

Zebra brochure entitled "Zebra® Z-Band® Direct Thermal Wristbands"; 2 pgs.; © 2007.

(Continued)

*Primary Examiner* — Syed A Islam
(74) *Attorney, Agent, or Firm* — Dicke, Billig & Czaja, PLLC

(57) ABSTRACT

A recipient verification system including a band having a pocket coupled to a strap. The pocket includes a first layer opposite a second layer. Seals are formed between the second layer and opposing side edges of the first layer to form an interior region. An end seal is formed adjacent a trailing end of the first layer and a liner covered adhesive coating is provided along an inner face of one of the layers. In an open arrangement, the liner is disposed over the adhesive coating, and a leading end of the first layer is free of the second layer to define an opening to the interior. In a closed arrangement, the liner is removed. The system can further include a separated insert. In an assembly state, the insert is insertable into the interior pocket, and a positive identification state, the insert is permanently affixed to the pocket.

35 Claims, 12 Drawing Sheets

U.S. PATENT DOCUMENTS

| | | | |
|---|---|---|---|
| 3,965,589 A * | 6/1976 | McDermott | 40/633 |
| 4,110,502 A | 8/1978 | Baer | |
| 4,199,882 A | 4/1980 | Clayman | |
| 4,226,036 A | 10/1980 | Krug | |
| 4,318,234 A | 3/1982 | Charles et al. | |
| 4,612,718 A | 9/1986 | Golub et al. | |
| 4,906,025 A | 3/1990 | Schreindl | |
| 4,914,843 A | 4/1990 | DeWoskin | |
| 4,951,970 A | 8/1990 | Burt | |
| 5,083,979 A | 1/1992 | Burt | |
| 5,129,682 A | 7/1992 | Ashby | |
| 5,225,162 A * | 7/1993 | Scoville | 422/401 |
| 5,242,053 A | 9/1993 | Rowe | |
| 5,457,906 A | 10/1995 | Mosher, Jr. | |
| 5,509,694 A | 4/1996 | Laurash et al. | |
| 5,581,924 A * | 12/1996 | Peterson | 40/633 |
| 5,653,472 A | 8/1997 | Huddleston et al. | |
| 5,933,993 A | 8/1999 | Riley | |
| 5,979,941 A | 11/1999 | Mosher, Jr. et al. | |
| 6,361,010 B1 | 3/2002 | Grosskopf et al. | |
| 6,474,694 B1 | 11/2002 | Emmert et al. | |
| 6,546,656 B2 | 4/2003 | Twentier | |
| 6,641,048 B1 | 11/2003 | Schintz et al. | |
| 6,655,063 B2 | 12/2003 | Goodin et al. | |
| 6,748,687 B2 * | 6/2004 | Riley | 40/633 |
| 6,766,039 B1 | 7/2004 | Al-Sheikh | |
| D496,405 S | 9/2004 | Stewart et al. | |
| D500,342 S | 12/2004 | Stewart et al. | |
| D500,524 S | 1/2005 | Stewart et al. | |
| D503,197 S | 3/2005 | Stewart et al. | |
| 6,971,200 B2 | 12/2005 | Valenti, Jr. | |
| 7,000,951 B2 | 2/2006 | Valenti, Jr. | |
| 7,137,216 B2 | 11/2006 | Ali et al. | |
| 7,240,446 B2 * | 7/2007 | Bekker | 40/633 |
| 7,454,855 B2 | 11/2008 | Kotik et al. | |
| 7,481,370 B2 | 1/2009 | Davis et al. | |
| 7,534,477 B1 | 5/2009 | Waggoner et al. | |
| 2004/0060216 A1 | 4/2004 | Riley | |
| 2004/0237367 A1 * | 12/2004 | Ali | 40/633 |
| 2004/0261644 A1 | 12/2004 | Stewart et al. | |
| 2005/0108912 A1 | 5/2005 | Bekker | |
| 2005/0184508 A1 | 8/2005 | Verden et al. | |
| 2006/0113788 A1 | 6/2006 | Riley | |
| 2006/0236578 A1 | 10/2006 | Saint et al. | |
| 2006/0254105 A1 | 11/2006 | Chang | |
| 2007/0120358 A1 | 5/2007 | Waggoner et al. | |
| 2008/0067802 A1 | 3/2008 | Bell et al. | |
| 2008/0301990 A1 | 12/2008 | McDermott | |
| 2008/0307685 A1 | 12/2008 | Ali et al. | |
| 2009/0094872 A1 | 4/2009 | Ali et al. | |
| 2009/0193701 A1 | 8/2009 | Greer | |

FOREIGN PATENT DOCUMENTS

| | | |
|---|---|---|
| GB | 1 538 105 | 9/1976 |
| GB | 2 067 506 A | 7/1980 |
| GB | 2 160 492 A | 12/1985 |

OTHER PUBLICATIONS

Zebra brochure entitled "Soft Infant Wristbands"; 1 pg.; © 2009.

* cited by examiner

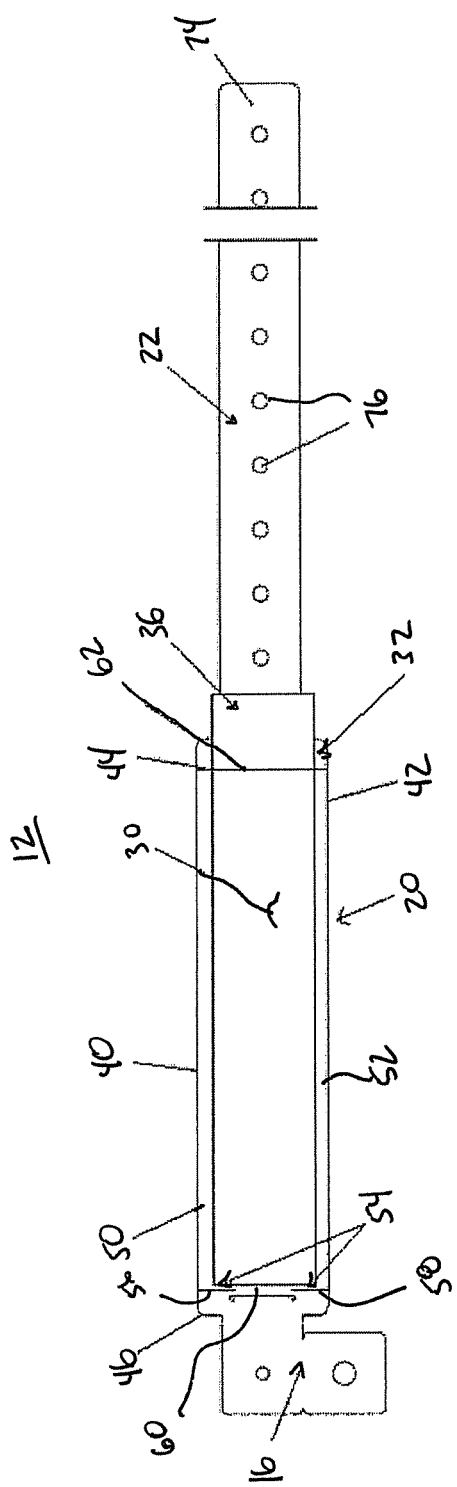
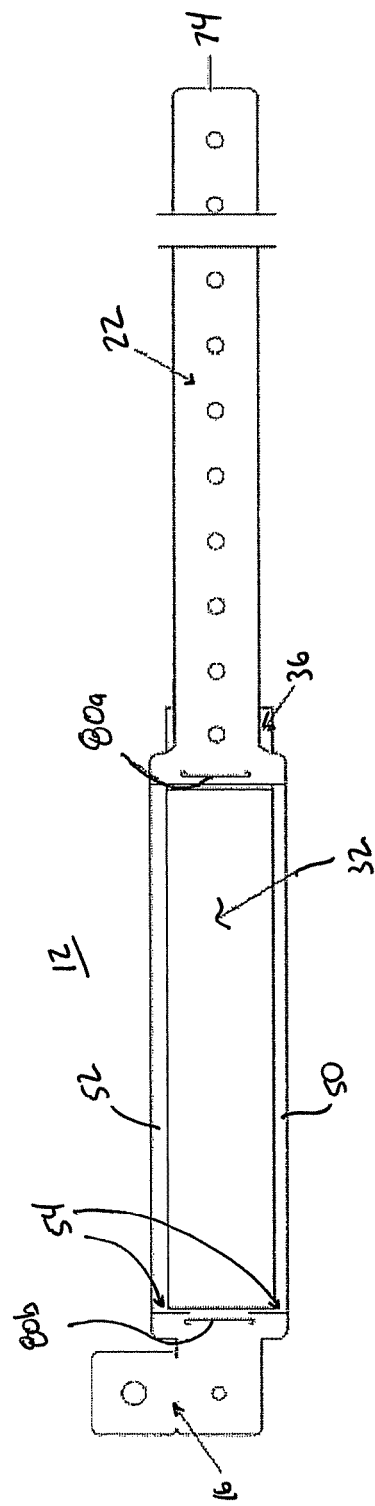
FIG. 2A
FIG. 2B

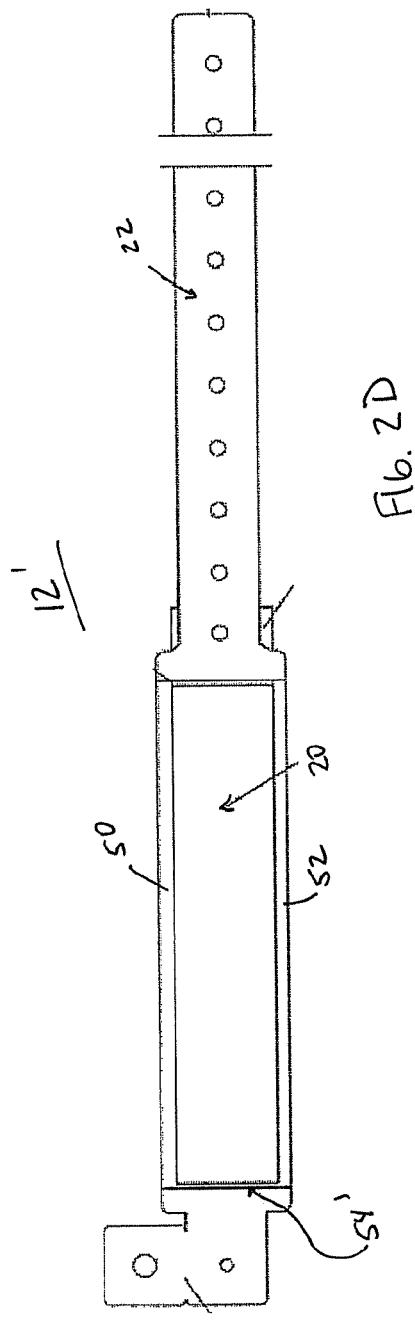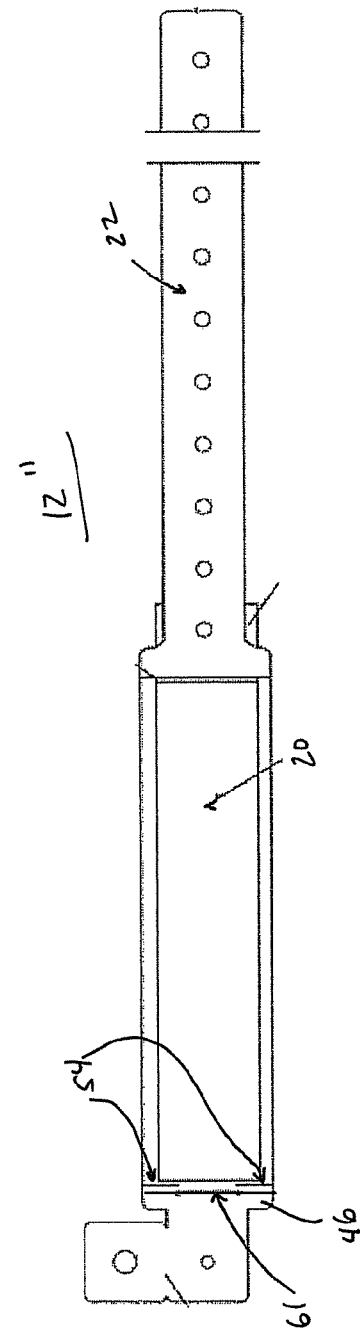

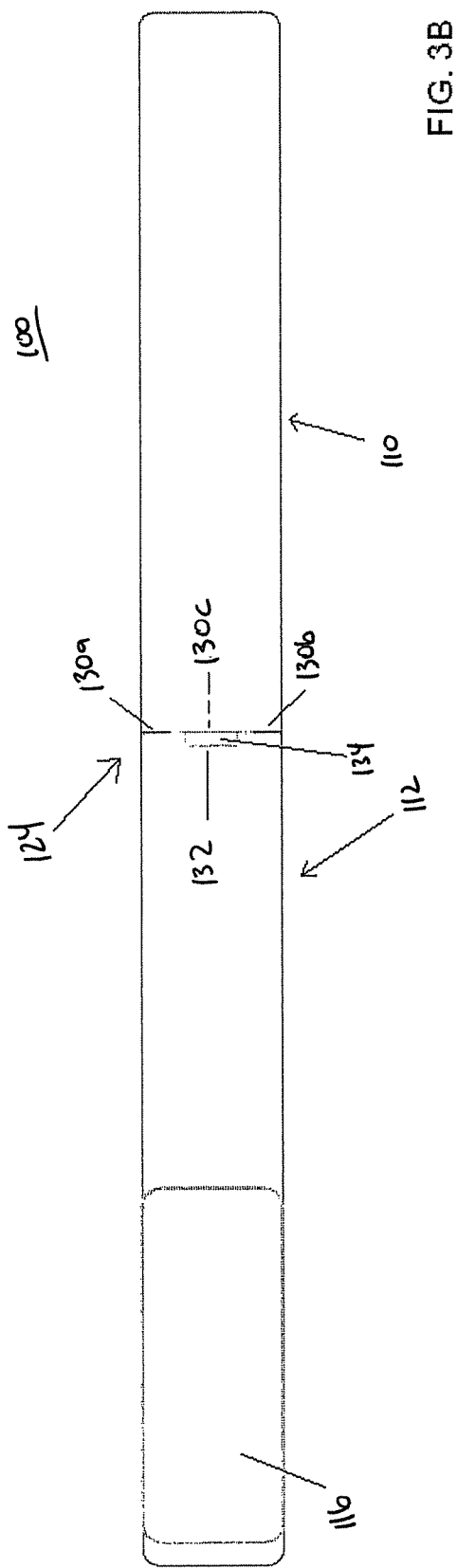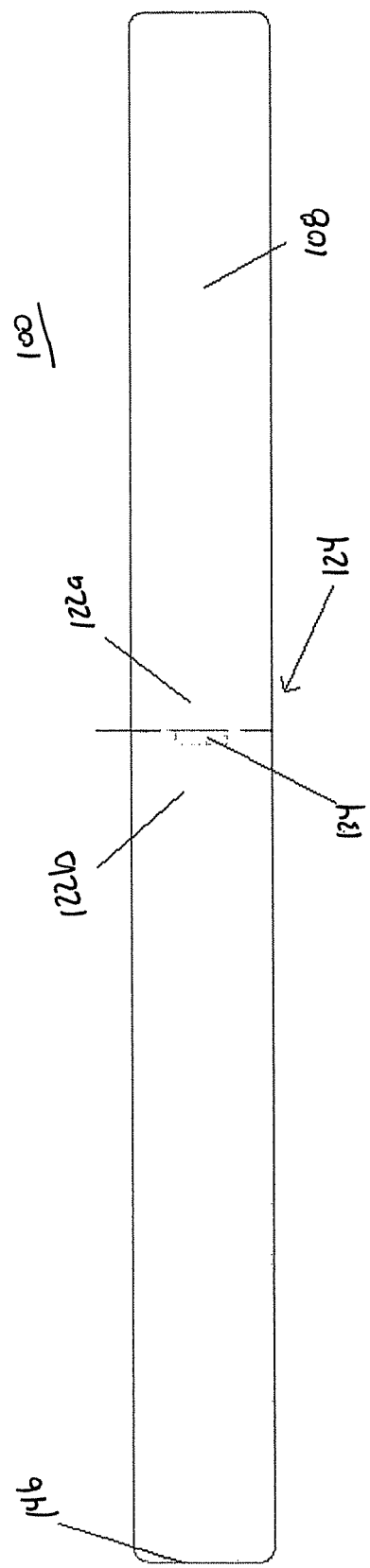

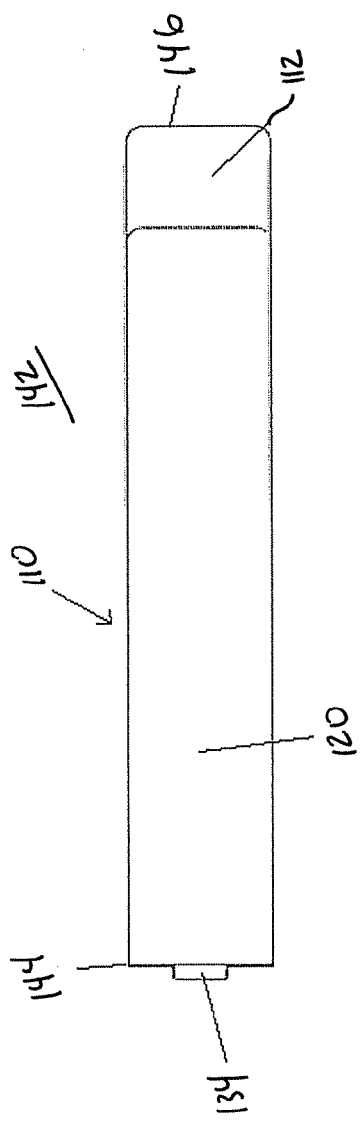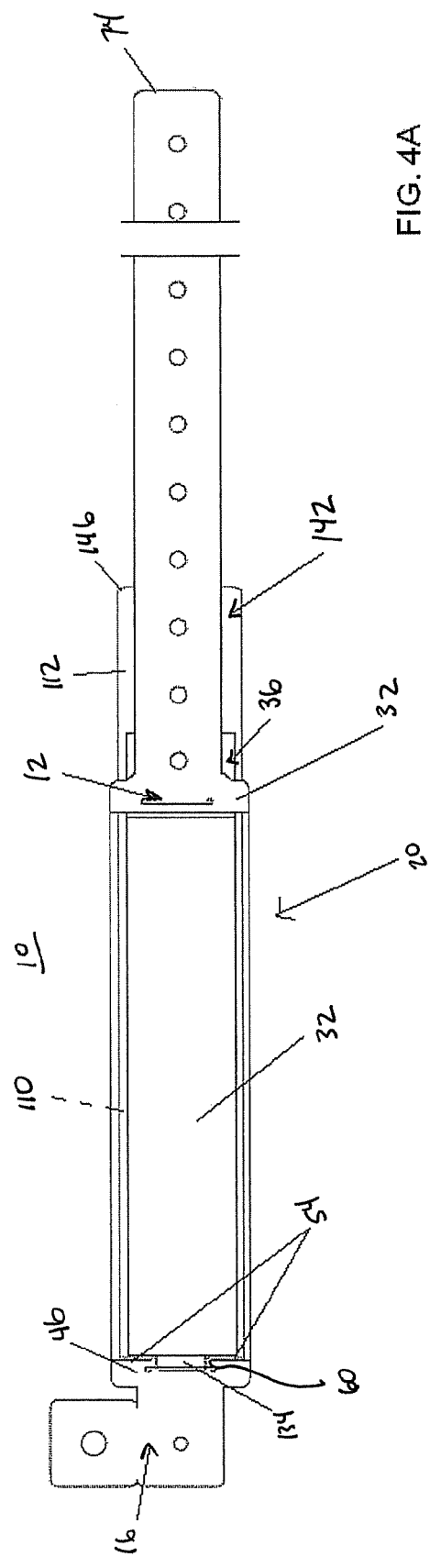

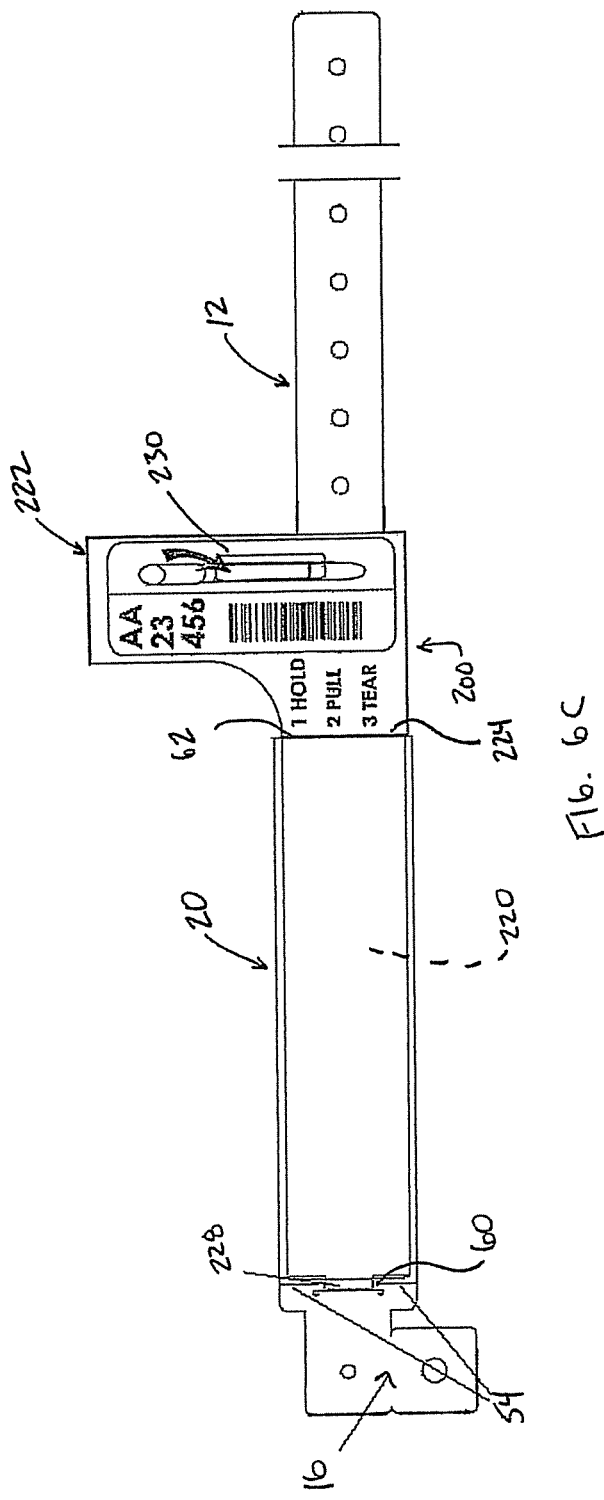

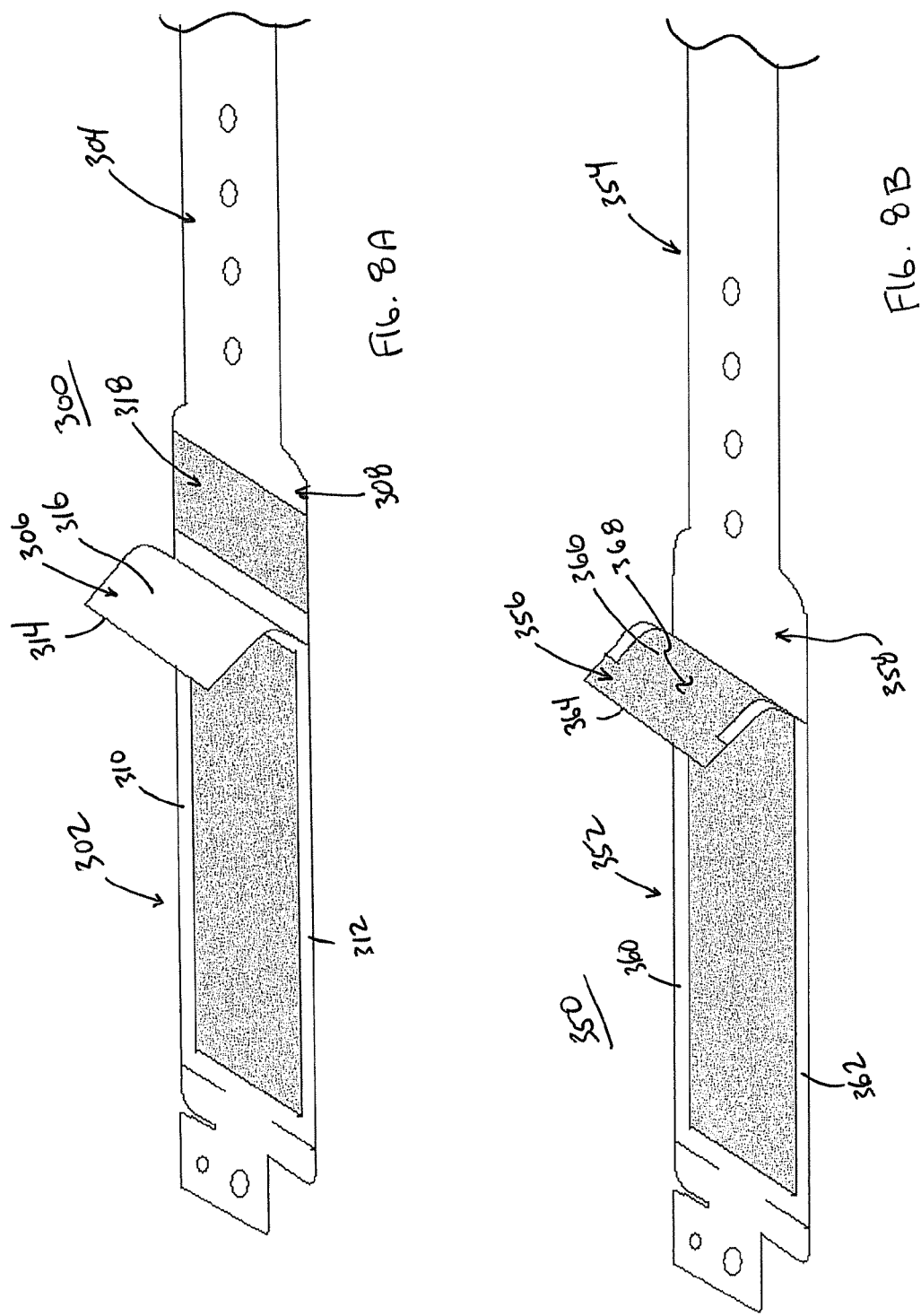

PATIENT IDENTIFICATION SYSTEMS AND METHODS OF USE, INCLUDING RECIPIENT VERIFICATION

CROSS-REFERENCE TO RELATED APPLICATIONS

This application claims priority under 35 U.S.C. §119(e)(1) to U.S. Provisional Patent Application Ser. No. 61/232,220, filed Aug. 7, 2009, entitled "Patient Identification Systems and Methods of Use, Including Recipient Verification", and bearing; the entire teachings of which are incorporated herein by reference.

BACKGROUND

The present disclosure relates to recipient verification systems, for example patient identification bands and related systems. More particularly, it relates to wearable identification bands for use in various environments, such as caregiver environments, that provide users with various labels and labeling methods, which can be linked to the wearer of the band, such systems being amenable for various end applications, and methods for making the same.

Positive patient identification occurs when a person's identifying information is physically attached to their person and is confirmed by being read by a caregiver. Many situations arise where a person may not accurately disclose their identity, may be unable to correctly identify themselves, or may be unconscious or unable to provide any identification. For such reasons, it is desirable to physically label individuals with their identity or other identifying information.

The need to assign a unique code or other identifier to a person or thing (collectively referred to as a "recipient") and subsequently employ the identifier in correlating other articles or activities to the recipient arises in a number of contexts. For example, positive patient identification is a critical step in providing medical treatment to patients in a caregiver environment (e.g., hospital). Commonly, an identification band is issued to the patient at the time of admission to the caregiver institution, and is worn by the patient at all times (e.g., a flexible plastic wristband or ankle band). The so-issued identification/admission band typically displays patient-related information (e.g., printed or labeled), such as name, date of birth, etc. In some instances, a unique patient identifier or other code is assigned to the patient and is displayed on the band, including, for example, bar code or numeric/alphanumeric code. The patient identifier can alternatively be supplied on a separate band (apart from the admission band), and is used to cross-reference other caregiver-related items with the patient via, for example, an electronic data base. The unique patient identifier provides an independent, physical link to the patient. For example, paperwork or other caregiver documents/medical charts relating to the patient may include the patient identifier. In addition, the patient identifier can be applied to specimen samples (e.g., test tubes for blood specimens) taken from the patient, or applied to therapeutic material(s) to be given to the patient, to better ensure that these and other items are accurately associated with the correct patient at all stages of the patient's visit with the caregiver institution. Along these same lines, similar recipient verification needs arise apart from hospital admission, for example blood banks, pharmacy, trauma centers, etc.

The information applied to a person must be provided in a format that can be read by the desired means (human readable, electronically readable, etc.). In addition, information must be generated at the time of use, or preexist at the time of use, and therefore is limited to handwriting, preprinted labels, imprinting, or other immediate printing means. This information must then be presented in a manner that can be connected to an individual. It must be easily assembled, applied to the person of interest, and withstand all exposure conditions that the person may encounter.

Disposable identification means have been created for this purpose. The most common form is a disposable band that can be applied to the wrist or ankle of a person. Such bands must be permanent and tamper evident once applied. In addition, they must endure exposure to sweat, bathing, and abrasion from daily activities, amongst other conditions. Due to the state and nature of the information to be applied, the wristband system must be designed to withstand the conditions of use.

There currently exist four main ways of creating disposable identification bands. With a first approach, an insert is created and is assembled within a pocket of the band. The pocket takes on many forms, such as, an opening within two layers of laminate, a tubular pocket, an open pocket assembled by means of a secondary layer, etc. The insert is assembled into the pocket and often the end of the pocket is sealed to secure and protect the insert. The insert can also be secured within the pocket by means of physical resistance. The second approach involves incorporating a layer of material that can be pressure exposed in order to display information. This layer of exposure material is laminated within the band structure. Lamination of the layer both secures and protects the exposure layer. When the user desires to customize the band with wearer information, the information is revealed by applying pressure to the exposure layer in the desired areas. The third technique involves adding an adhesive layer over the applied information. Information is applied to the band by means of handwriting, preprinted label/sticker, imprinting or equivalent means. Then a clear laminate with adhesive is actuated and sealed over the applied information to both secure and protect it. The fourth approach employs the use of a form. A band structure is formed and cut into a printable form. The wearer information is applied to the form by passing it through a printer. This act immediately secures the information to the band as it is directly printed on. Then, the band is removed from the form and self-laminates with a clear adhesive layer. In essence, the printed label becomes the band itself.

Each of these four described methods suffers from either lack of permanence of the band structure itself or lack of durability when exposed to environmental conditions. Pocket bands retain the information by means of resistance fit or seal; if tampered with, the information can be easily removed and perhaps even replaced. Also, the pocket seal is imperfect and with exposure to abrasion and liquids, the pocket eventually fills and retains moisture that degrades the housed information. Bands whose information is formed from within, by exposure to pressure, provide excellent permanence of the applied information and protection to the environment; however, as the band is worn and exposed to the rigors of daily wear, all of the exposure material becomes activated and the information becomes illegible over time. Information secured and protected by a clear adhesive shield suffers from the vulnerability of the adhesive seal. The edges of the adhesive are able to be lifted and weaken by the user as well as the environment. Poor alignment of applied information labels can also lead to a compromised seal. Once the seal has been compromised, information can be removed or damaged by liquid exposure. Lastly, in the case of the form/information label that becomes the band itself—this type of product suffers from limitations on the band side. Many compromises are made to ensure that the form material can be printed, cut, and laminated. This reduces the comfort, durability, and allowable length of the band itself.

SUMMARY

Features of the present disclosure provide ways to both firmly secure and adequately protect an insert within a band system. Unlike the existing art, this system provides a means for quick and easy assembly, secures and protects the applied information from user removal or tampering, seals the information from environmental abrasion and liquid exposure, and allows for the band properties to be maximized by utilizing a separate band structure.

The disclosed system offers other advantages, such as improved comfort and cleanliness due to lack of liquid retention. Additionally, the system can accommodate all types of generated patient information as well as independently generated unique identifiers. This system also offers advantages to recipient verification systems including, but not limited to, the ability to physically attach a specimen tube or recipient related item label to the band information label and in turn, the band.

BRIEF DESCRIPTION OF THE DRAWINGS

FIG. 2A is a front plan view of a band component of the system of FIG. 1 in an open arrangement;

FIG. 2B is a rear plan view of the band of FIG. 2A;

FIG. 2D is a front plan view of another band useful with the system of FIG. 1;

FIG. 2E is a front plan view of another embodiment band useful with the system of FIG. 1;

FIGS. 3B and 3C are front and rear plan views, respectively, of the insert of FIG. 3A, with printed portions omitted;

FIG. 3D is a top plan view of the insert of FIG. 3A in a folded arrangement;

FIGS. 4A and 4B are front and rear plan views, respectively, of the verification system of FIG. 1 in a positive identification state;

FIG. 6C is a simplified top plan view of a recipient verification system in accordance with principles of the present disclosure and in a positive identification state, including the band of FIG. 2A and the insert of FIG. 6A;

FIG. 8A is a simplified perspective view of a portion of another band useful with the recipient verification system of FIG. 1; and FIG. 8B is a simplified perspective view of a portion of another band useful with the recipient verification system of FIG. 1.

DETAILED DESCRIPTION

Aspects of the present disclosure relate to recipient verification systems useful in a variety of different environments. For example, the recipient verification systems of the present disclosure can be used in medical or patient-related contexts, such as with patient admission to a hospital (and related medical records, charts, items (e.g., clothing), etc.), testing or specimen drawing (e.g., X-rays, blood specimen, DNA specimen, organ donation, stem cell specimen, fertilized eggs, etc.) entirely apart from (or as part of) a hospital stay, blood banks, pharmacies (e.g., custom chemotherapy drugs, nuclear pharmacy, labor and delivery, etc.), or other instances in which patient identification is needed. Other applications are equally appropriate, such as police or security situations in which a number of individuals must be quickly processed on-site, ticketing applications, etc. Thus, while several of the examples described below mention patient identification, as well as hospital admission, the systems and methods of the present disclosure are in no way limited.

Figure 1:
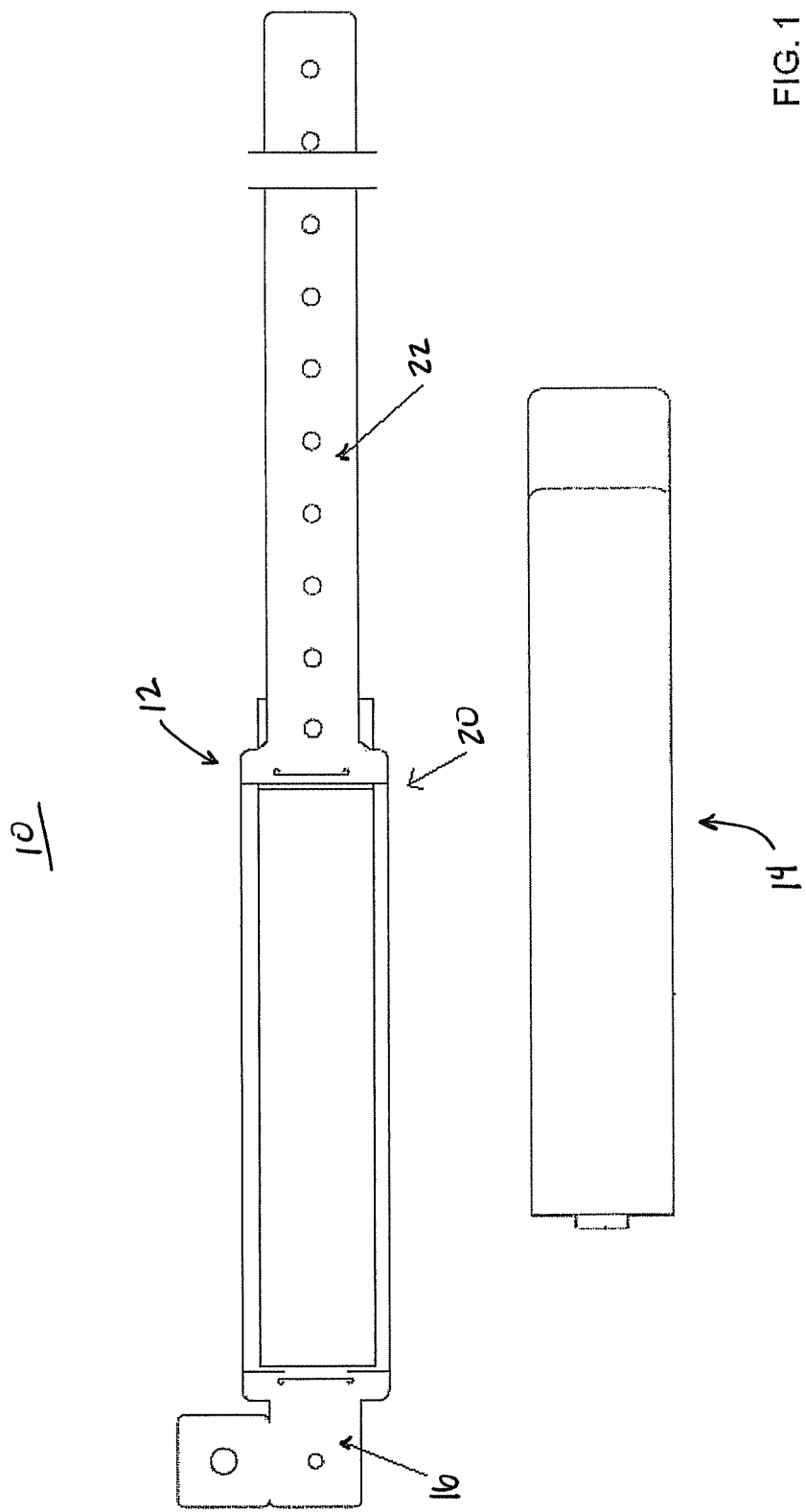
FIG. 1 is an exploded top view of a recipient verification system in accordance with principles of the present disclosure.

One embodiment of a recipient verification system 10 in accordance with principles of the present disclosure is shown in FIG. 1. The recipient verification system 10 includes a band 12, an insert 14 that can be incorporated into the band 12, and an optional closure device 16 (referenced generally) that can employ a tamper-evident connection. Each of the components is described in greater detail below. In general terms, however, the band 12 and the insert 14 are formed apart from one another and are separately provided to a user (e.g., healthcare facility). The system 10 is transitionable from an assembly state to a positive identification state. In the assembly state, the insert 14 is separated from the band 12 and can receive recipient information. In the positive identification state, at least a portion of the insert 14 is permanently attached to the band 12 (e.g., adhesively bonded or laminated), with the band 12 being available for securement to the recipient's appendage via the closure device 16. The insert 14 carries identification information that may be unique to the recipient. In other embodiments, recipient verification systems of the present disclosure consist only of the band 12 and optionally the closure device 16.

The band 12 can assume a variety of forms and generally includes a pocket 20 and a strap 22. The strap 22 is configured for placement about a wearer's appendage, and the pocket 20 is coupled to the strap 22. As used throughout this disclosure, a "pocket" (e.g., the pocket 20) is in reference to the coupled arrangement of two (or more) opposing material layers combining to define an interior pocket region within which items (e.g., the insert 14) can be attached to and protected by the band 12.

Figure 2C:
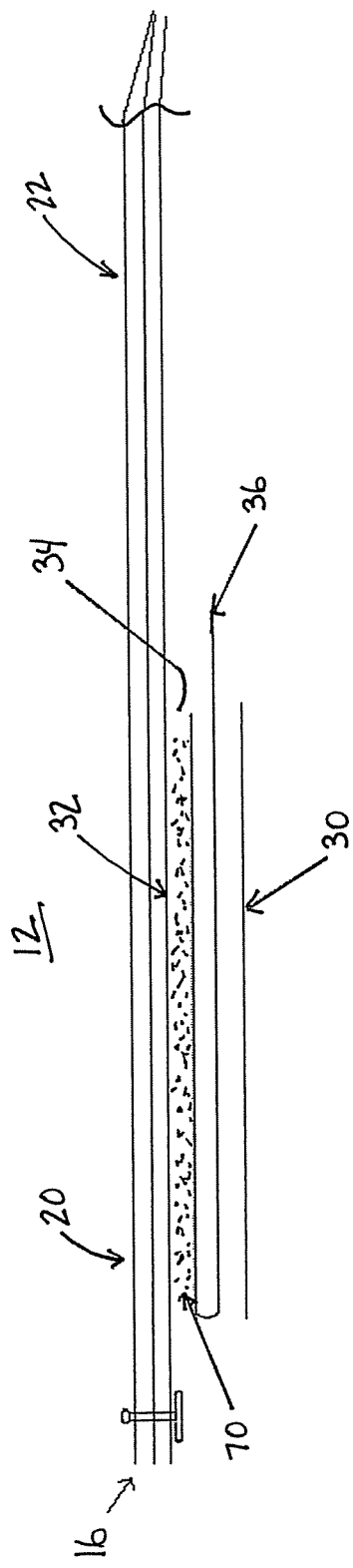
FIG. 2C is a simplified, enlarged side view of the band of FIG. 2B.

The band 12, including the pocket 20, is shown in greater detail in FIGS. 2A-2C. The pocket 20 includes opposing, first and second layers 30, 32 connected to one another as described below to define an interior pocket region 34 (best shown in FIG. 2C). As a point of reference, the pocket 20 is transitionable from an open arrangement (reflected in FIGS. 2A-2C) in which the interior pocket region 34 is open and easily accessible (e.g., for insertion of the insert 14 (FIG. 1)), to a closed arrangement (not shown) in which the interior pocket region 34 is less open (e.g., fully closed in some embodiments) and not easily accessible (e.g., liquids cannot readily enter the interior pocket region 34). In the open arrangement, a release liner 36 is disposed between the layers 30, 32 as described below.

The opposing material layers 30, 32 are connected to one another in various fashions (e.g., adhesively bonded, etc.) to generally define a perimeter of the pocket 20. The opposing material layers 30, 32 may be composed of a variety of transparent materials (e.g. for the layer displaying the desired user verification information) or opaque materials (e.g. for the layer comprising the back side of the pocket 20). A shape of the pocket perimeter can assume a variety of forms, and can be akin to the rectangular shape as shown. With specific reference to FIG. 2A, the pocket perimeter shape is generated primarily by the first layer 30, and by regions of sealing between the first and second layers 30, 32. With this in mind, the first layer 30 can generally be viewed as having or defining opposing first and second sides 40, 42 and opposing leading and trailing ends 44, 46. With these conventions in mind, pockets in accordance with the present disclosure can include a first side seal 50 formed between the first side 40 and the second layer 32, a second seal 52 between the second side 42 and the second layer 32, and an end seal 54 between the layers 30, 32 adjacent the trailing end 46 (i.e., the end seal 54 can be in contact with the trailing end 46, or can be slightly spaced from the trailing end 46). In some embodiments, the end seal 54 can be described as including opposing seal segments 56, 58 extending adjacent the trailing end 46 from the corresponding side seal 50, 52. The seal segments 56, 58 are separated by a gap 60, thereby defining the end seal 54 as an intermittent or discontinuous seal. In a related embodiment band 12' shown in FIG. 2D, the end seal 54' is complete, extending continuously between the side seals 50, 52. In yet another related embodiment band 12" of FIG. 2E, a primary end seal 61 is formed adjacent the trailing end 46 in addition to the partial seal 54. The primary end seal 61 is longitudinally spaced from the partial end seal 54, and is closer to the trailing end 46. The partial end seal 54 is discontinuous or intermittent as described above; the primary end seal 61 is between the partial end seal 54 and the trailing end and is continuous or complete, establishing a water tight-like seal.

Returning to FIGS. 2A-2C, in at least the open arrangement, the leading end 44 is free of bonding to the second layer 32 (for example due to the presence of the liner 36), thereby defining an insert opening 62 to the interior pocket region 34 at which the pocket 20 is open and accessible. The closed or partially closed end 46 of the pocket 20 can, in some embodiments, be formed within the band 12 so that the total pocket 20 is sealed on one end, but can have various partial seals formed at the closed end 46 to create shapes within the pocket 20. In additional embodiments, the roles of the ends 44, 46 can be reversed and the pocket 20 may open towards the closure 16.

The first pocket layer 30 as shown in FIG. 2C can form the pocket 20 in a variety of ways. The first pocket layer 30 can be a direct extension of the second layer 32 and folded to create the pocket 20, or a separate laminate of material that is sealed to the second layer 32 that is otherwise provided as in integral material extension of the strap 22. Alternatively the pocket 20 can be comprised of two opposing materials sealed together that are attachable to (e.g. via an adhesive or cinch design), but non-contiguous with, the strap 22 (or other base material of the band 12). In summary, pockets in accordance with the principles of the present disclosure can consist of two opposing sides/layers with neither, one, or both of the opposing sides/layers being initially contiguous with material of the strap 22. Consistent with this understanding, the term "seal" as used throughout this specification (e.g., "side seal," "end seal," etc.) includes two discrete layers bonded to one another (e.g., heat, ultrasound, adhesive, etc.), or a single layer folded onto itself, with the fold line constituting a "seal" in accordance with the present disclosure.

As shown in the orientation of FIG. 2A, the first pocket layer 30 is positioned on the front side of band 12, facing away from the wearer's appendage when the band 12 is in use/worn. In this embodiment, the insert opening 62 of the pocket 20 is readily accessible while the band 12 is wrapped around the user's appendage. Alternatively, in accordance with the principles of the present disclosure, the first pocket layer 30 shown in FIG. 2A can be positioned on the back side of the band 12, facing the user's appendage during use. In this embodiment, the insert opening 62 of the pocket 20 is subsequently also positioned towards the wearer's appendage when the band 12 is in use, enabling information within the pocket 20 to be less susceptible to environmental damage (e.g. via water exposure, etc.).

The insert opening 62 of the pocket 20 in accordance with principles of the present disclosure can likewise be constructed in a variety of manners. In the embodiment depicted in FIGS. 2A-2C, the insert opening 62 is formed or defined by an absence of bonding between the base or second layer 32 relative to the first pocket layer 30. Alternatively, in constructions in which the two opposing layers 30, 32 comprising the pocket 20 are fully sealed around their overlapping perimeter, the insert opening 62 can be formed via an opening (e.g. a cut or slot) through one of the opposing layers 30 or 32, with the opening enabling access to the interior pocket region 34.

In order to attach/secure an insert (e.g., the insert 14 of FIG. 1) to the band 12 for displaying wearer identification, the pocket 20 includes an adhesive coating or layer 70 as shown in FIG. 2C. The adhesive layer 70 may be applied to the inner face of one or both of the first layer 30 and/or the second layer 32. The adhesive coating 70 is used to adhere the inner face of one or both of the pocket layers 30, 32 to a variety of inserted information bearing materials, including pre-printed labels, pre-packaged inserts, barcodes, etc. As shown in FIG. 2A-2C, the adhesive layer 70 may be obscured by the detachable release liner 36 or equivalent means in the open arrangement, the removal of which would then enable the adhesive layer 70 to laminate to the insert 14. Such lamination results not only in attachment of the insert 14 to the band 12, but also protection of the information provided on the insert 14 from environmental degradation (e.g. water, etc.). The adhesive layer 70 may be applied to the band 12 in a variety of ways or may be an integral portion of one of the pocket layers 30, 32. In some embodiments, the adhesive coating 70 encompasses an entirety of the inner face of the corresponding pocket layer(s) 30, 32; in other embodiments, the adhesive coating 70 covers only a portion of the corresponding inner face.

To ensure that the recipient information contained within the band insert 14 (FIG. 1) is completely adhered to the adhesive layer 70 described above, it is can be useful to effectively align the insert within the pocket 20. This alignment is better enabled by ensuring that the band pocket 20, and in particular the interior pocket region 34, has dimensions commensurate with the size of the insert (e.g., the insert 14 of FIG. 1) to be attached inside the pocket 20. This similarity in dimensions between the pocket 30 and the insert 14 minimizes undesired lateral motion or skewing (relative to the opposing side seals 50, 52) that the insert may experience within the pocket 20 prior to being adhered. Stated otherwise, a shape of each of the side seals 50, 52 corresponds with a shape of the insert side edges (e.g., linear), and a transverse distance between the side seals 50, 52 is slightly greater than a width of the insert 14.

As shown in the band embodiment depicted in FIG. 2A, longitudinal alignment is achieved, and thus excessive longitudinal motion of the insert 14 (FIG. 1) is avoided, via the partial end seal 54 of the pocket 20. In practice, upon insertion of an insert into the pocket 20 (via the insert opening 62), the insert is pushed through the length of the interior pocket region 34 until it encounters the partial end seal 54 and is subsequently halted. The partial end seal 64 thereby ensures that the insert is optimally positioned against the pocket adhesive layer 70 in the longitudinal direction and that the insert will be better laminated and protected upon removal of the band release liner 36.

In general terms, the strap 22 is adapted for placement about a user's wrist, ankle or other appendage. As a point of reference, FIGS. 2A (front view) and 2B (back) illustrate the recipient verification band 12 prior to insert assembly and placement about the user's appendage. The strap 22 can be formed in-line with, and extend from, the second pocket layer 32. In this regard, the strap 22 can have any desired length appropriate for a desired end-user (e.g., patient). For example, a length of the strap 22 (in combination with a length of the pocket 20 and closure 16) can range from a larger size appropriate for placement about an adult's wrist or ankle, to a smaller size appropriate for use with children or infants. In other embodiments, the strap 22 can be modified by a caregiver (or other third party) immediately prior to use in an attempt to better match a size of the user or patient in question, for example by cutting the strap 22 (adjacent a tail end 74) to a desired length. To facilitate this approach, the strap 22 can optionally include or display indicia, openings 76 or weakened points designating lengths and/or possible cut locations.

In general, the recipient verification band 12 and its components can be formed and assembled in a variety of manners. In the embodiment depicted in FIGS. 2A-2C, the band 12 is defined as a die-cut, single- or multi-layer laminate structure. The laminate material(s) are selected to be flexible, resistant to tearing, and appropriate for contact with human skin. For example, acceptable laminate material(s) include polyethylene, polyester, vinyl, non-woven foams, low density polyethylene/COC blends, Tyvek®, etc. In the embodiment depicted in FIGS. 2A-2B, the band 12 is cut from a single laminate structure to include the strap 22, the second pocket layer 32, and the first pocket layer 30. In this embodiment, the components are formed as a homogenous material (e.g., formed by at least one common, continuous material web). In an alternative embodiment, the components may be formed of differing materials (e.g., the second pocket layer 32 can be opaque whereas the first pocket layer 30 can be substantially transparent, or vice-versa).

As shown in FIGS. 2A-2C, the closure device 16 of the recipient verification system 10 described in the present disclosure consists of a snap closure mechanism that provides a permanent lock via the connection of the closure's male and female ends. In accordance with the principles of the present disclosure, the closure device 16 can be manifest as a variety of different mechanical or adhesive permanent locking mechanisms.

Modification of the recipient verification band 12 with a replacement strap may be desirable under various circumstances, such as when the strap 22 is damaged or is uncomfortable when worn by the wearer (e.g., is secured too tightly about the patient's wrist), etc. Under these and other scenarios, the caregiver or other third party user may desire to employ a new or replacement strap for the recipient while not being required to generate new recipient identification information and corresponding label(s). In some embodiments, optional first and second slits or slots or passages 80a, 80b are formed at opposite sides of the pocket 20, in relatively close proximity thereto. The slots 80a, 80b serve as part of a band replacement feature as described in U.S. application Ser. No. 12/465,449 filed May 13, 2009 and entitled "Recipient Verification Systems and Methods of use, Including Patient Identification"; the entire teachings of which are incorporated herein by reference. While the slots 80a, 80b are illustrated as being closed-ended slots, other configurations are also acceptable (e.g., holes, perforations, etc). In yet other embodiments, the slots 80a, 80b are omitted.

Returning to FIG. 1, the insert 14 can assume a wide variety of forms configured for assembly to the pocket 20. One embodiment of an information bearing insert 100 for use with the above described recipient verification system 10 is illustrated in FIG. 3A-3D. The insert 100 includes or defines opposing first and second ends 102a, 102b, opposing first and second sides 104a, 104b, a top printable facestock layer 106, and an underlying release liner layer 108 as shown in the rear view of the insert in FIG. 3C. The insert 100 is comprised of at least two contiguous regions including: an information bearing area 110 and an insert guiding area 112. In some embodiments, the insert guiding area 112 contains instructions for use 114 and a first removable sticker 116 for use with recipient related items. In this embodiment shown in FIG. 3A, both the information bearing area 110 and insert guiding area 112 are printed with identical indicia 118 that allow the wearer to be associated with items that are labeled with the removable sticker 116. When in use, the insert 100 may be presented as either an independent entity or as a part of a pre-printed form from which the insert 100 can be detached. A detailed description of the two major regions comprising this insert embodiment is provided in subsequent paragraphs.

The information bearing area 110 of the insert 100 includes both a unique, pre-printed patient identifier 118 and a patient information region 120 to which patient information can be transcribed or adhered to via an externally generated label. A first opposing edge 122a of the information bearing area 110 separates this area from the insert guiding area 112. In one embodiment of the information bearing area 110, there exists a foldable region 124 between the first opposing edge 122a of the information bearing area 110 and the corresponding opposing edge 122b of the insert guiding area 112. During insertion of the information bearing insert 100 into its band (e.g., the band 12 of FIG. 1), the foldable region 124 facilitates the alignment and insertion of the information bearing area 110 within the band pocket 20 (FIG. 2A).

Figure 3A:
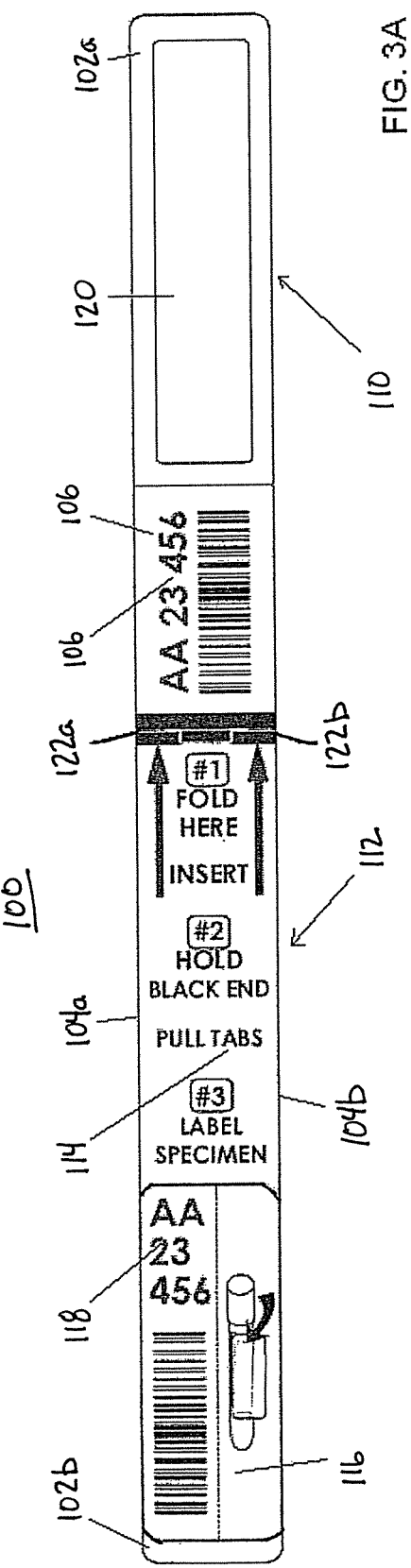
FIG. 3A is a top plan view of an insert component of the system of FIG. 1 and in an unfolded arrangement.

The insert guiding area 112 depicted in FIG. 3A contains the instructions 114 pertaining to the use of the insert 100. As shown in this embodiment, the instructions 114 are not limited to written descriptions but may contain visual illustrations and other means depicting the use of the insert 100 or desired information. Additionally, as depicted in FIG. 3A, the insert guiding area 112 may also contain the detachable identification label or sticker 116 that can be adhered or attached to other belongings or specimen desired to be associated with the recipient/wearer. Such detachable identification label 116 may include both the unique patient identifier 118 (corresponding to the identifier 118 located on the information bearing area 110) and the instructions 114 describing how to appropriately apply the label 116. In embodiments where the identification label 116 is to be adhered to specimens or other belongings of the recipient/wearer of the insert, the identification label 116 is removable along its perimeter, enabling the label 116 to be peeled off from an underlying release liner 108 (FIG. 3C) and adhered as needed.

The identification label 116 described above may be embodied in a variety of manners in accordance with the principles of the present disclosure. In one embodiment, the identification label 116 can be comprised of a plurality of detachable labels that can be applied to multiple objects associated with the verification system recipient or wearer. In another embodiment, the identification label 116 can be folded behind, rather than detached from, the insert information bearing area 110 prior to insertion of the information bearing area 110 into the band pocket 20 (FIG. 2A). This embodiment would thereby enable the identification label 116 to remain temporarily contained and protected by the band pocket 20 until use.

In one embodiment of the information bearing insert 100 depicted in FIGS. 3A-3D, the first opposing edge 122a of the information bearing area 110 contains a series of partial die cuts 130a, 130b (through the thickness of face stock 106) and full die cuts 132 (through the face stock 106 and release liner 108) on its front surface around the perimeter of a tab 134, as depicted in FIG. 3B. The first opposing edge 122a also contains additional partial die cuts 130c (through the release liner 108) on its back surface along the length of the tab 134, as depicted in FIG. 3C. Collectively, this combination of partial die cuts and full die cuts enable the insert guiding area 112 to be detached from the information bearing area 110 while simultaneously removing the release liner 108 of the information bearing area 110.

In practice, prior to placing the insert 100 into its band, the user bends the foldable portion 124 of the insert 100 along a fold line 140 (FIG. 3C), resulting in the folded insert 142 depicted in FIG. 3D. The folded insert 142 defines first and second opposing ends 144, 146. In the folded state, the tab 134 protrudes from the first end 144 with dimensions commensurate with the gap 60 between the partial pocket seal segments 56, 58 depicted in FIG. 2A.

Figure 4B:
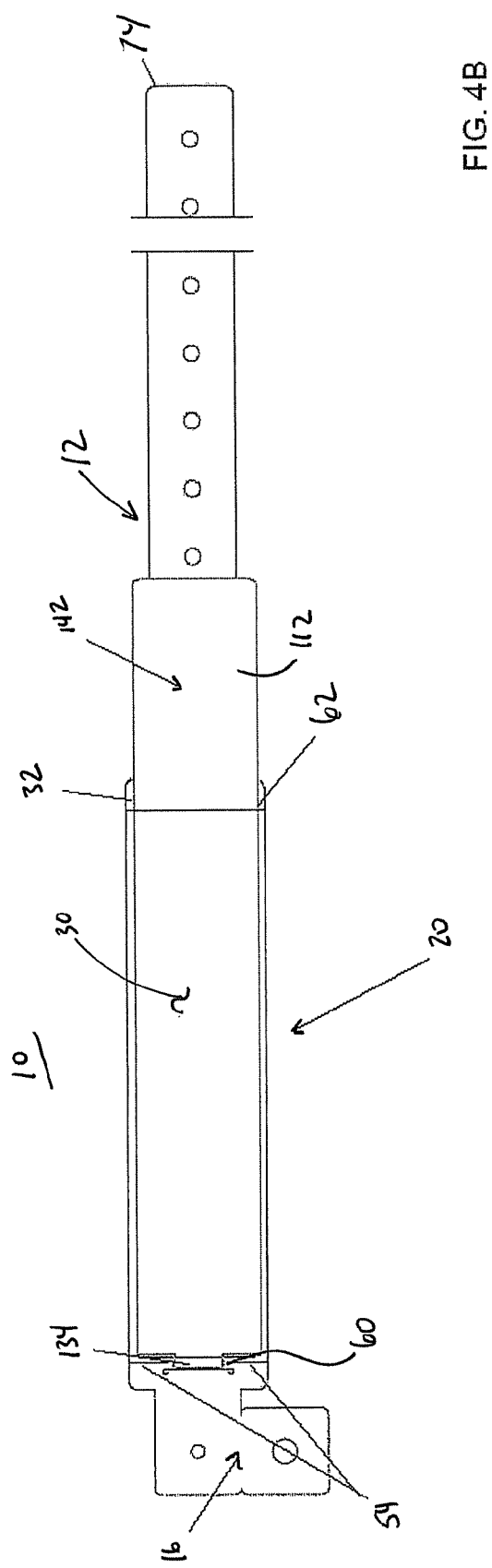

As is depicted in FIG. 4A, that otherwise reflects an assembly state of the system 10, the folded insert 142 is inserted (with insert information bearing area 110 facing towards the user) into the interior pocket region 34 (FIG. 2C) between the release liner 36 and second pocket layer 32. Upon entering the band pocket 20, the folded insert 142 is pushed further into the pocket 20 until the insert 142 contacts the partial end seal 54 at the pocket's trailing end 46. As depicted in FIGS. 4A and 4B, the protruding tab 134 of the insert 142 passes through the gap 60 and protrudes slightly beyond the partial end seal 54. To transition the system 10 to the positive identification state, the user subsequently holds the protruding tab 134 to keep the folded insert 142 in place while pulling the band release liner 36 and the insert guiding area 112 at end 146. This action in turn adheres the information bearing area 110 to the inner face of the second pocket layer 32 while simultaneously adhering the face stock 106 of the information bearing area 110 to the inner face of the first pocket layer 30.

The insert adhesion method described above can alternatively be accomplished in two steps. For example, following adhesion of the information bearing area 110 to the band 12 by removal of the adhesive liner 36, the user can then detach the insert guiding area 112 from the remainder of the folded insert 142 by pulling the end 146 of the insert guiding area 112 out of the pocket 20 and away from the tab 134. Due to the nature of the cuts 130a-130c, 132 (FIG. 3C) on the first opposing end 122a as described above, removal of the insert guiding area 112 simultaneously removes the insert release liner 108 (FIG. 3C) behind the information bearing area 110. Upon removal of the patient identification area release liner 108, the user then is able to adhere the back side of the information bearing area 110 to the inner face of the first pocket layer 30 of the band 12.

In summary, the recipient verification systems described above provides a means to adhere both the front and back sides of the insert information bearing area 110 to the band 12, thereby enabling the area to be maximally protected from environmental degradation in the positive identification state. In other embodiments described below, separate adhesive is omitted from the insert 146, such that a single face of adhesion is provided. With the insert guiding area 112 separated from the information bearing area 110, the detachable recipient identification label 116 can be further separated from the insert guiding area 112 and applied to specimens and belongings associated with the band wearer/recipient, as described earlier.

Figure 5:
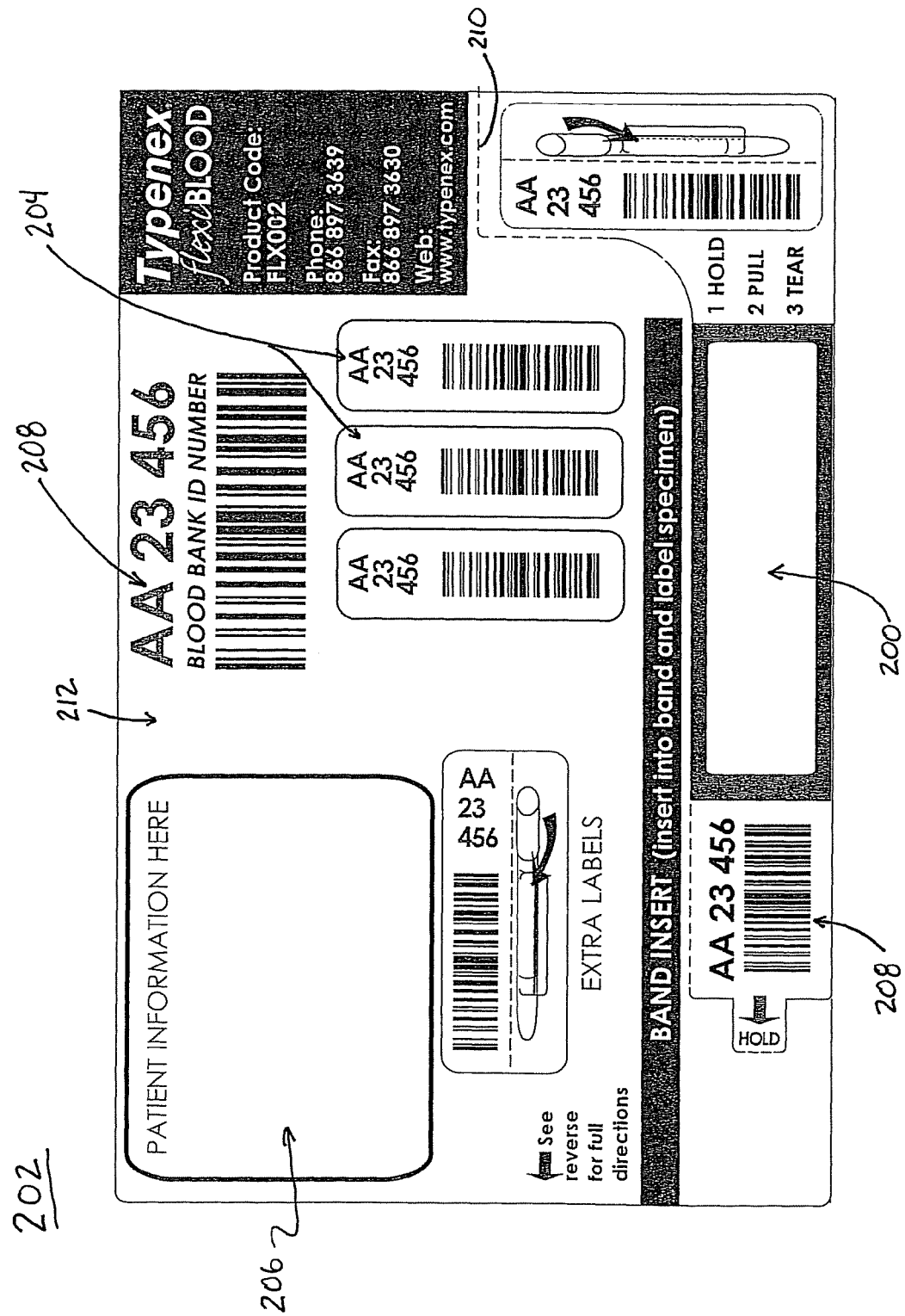
FIG. 5 is a front plan view of a form including an insert useful with the recipient verification system of FIG. 1.

Another embodiment of an insert 200 useful with the recipient verification system 10 (FIG. 1) is shown in FIG. 5. As a point of reference, the insert 200 is initially formed as part of a form 202 that may be part of the corresponding identification system. In general terms, the form 202 is created by printing and applying partial cuts to a label stock material. In addition to the insert 200, the form 202 can include or incorporate various other features, such as one or more removable labels 204 and an information zone 206. A unique identifier or indicia 208 (e.g., alphanumeric, bar code, etc.) is displayed at multiple locations along the form 202, including the insert 200 and the labels 204. Regardless, intermittent die cuts 210 (referenced generally) are formed through a thickness of the form 202 to define the insert 200 apart from a remainder 212 of the form 202. With this construction, then, the insert 200 is removable from the remainder 212 of the form 202 for subsequent assembly to the separate band (e.g., the band 12 of FIG. 1). In other embodiments, the insert 200 can be provided as a standalone structure (e.g., the insert 200 is not provided as part of a separate form).

Figure 6A:
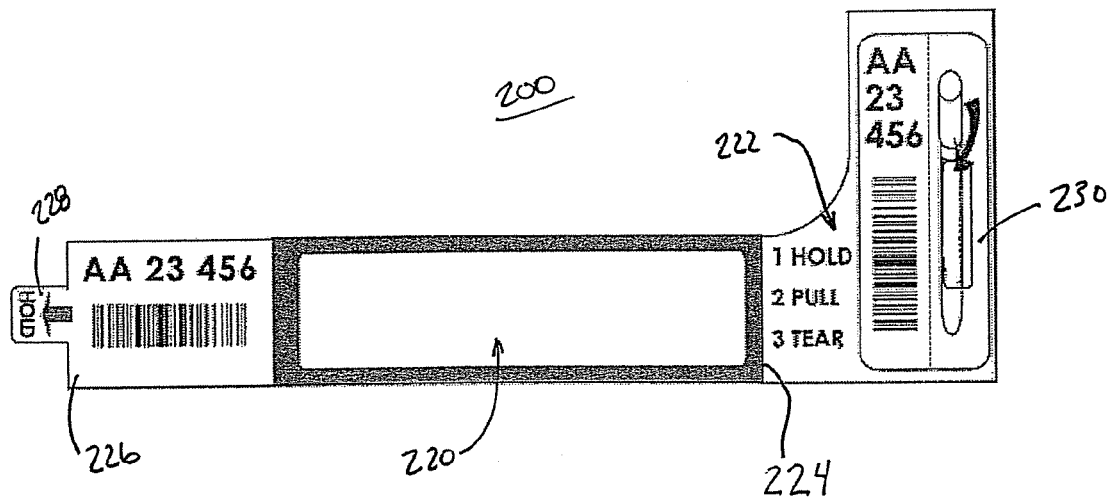
FIG. 6A is an enlarged view of the insert of FIG. 5.
Figure 6B:
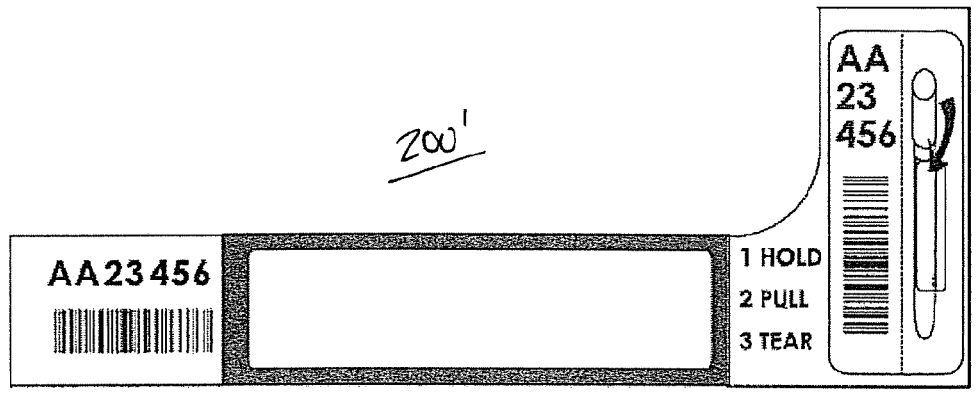
FIG. 6B is an enlarged view of another insert useful with the recipient verification system of FIG. 1.

The insert 200 is shown in greater detail in FIG. 6A, and generally includes or defines a base portion 220 and a label portion 222. The portions 220, 222 are integrally formed, but are separable from one another along a die cut or perforated tear line 224. The base section 220 extends from the tear line 224 and terminates at an insertion end 226. In general terms, the base section 220 is sized and shaped in accordance with a size and shape of the pocket 20 (FIG. 2A), with the insertion end 226 optionally forming a tab 228. The alternative insert 200' of FIG. 6B is highly similar, except that the tab 228 (FIG. 6A) is omitted. Returning to FIG. 6A, the label portion 222 generally extends in an opposite direction from the tear line 224, and optionally includes a removable insert label 230. In some embodiments, the label portion 222 extends transversely relative to the base section 220, resulting in the L-like shape as shown. Alternatively, however, other shapes are also envisioned.

During use, desired recipient information can optionally be added to the base section 220. The so-prepared insert 200 is then assembled to the band 12 as described above and as shown in FIG. 6C. In particular, the base portion 220 (generally hidden in the view of FIG. 6C) is inserted into the pocket 20 (in the open arrangement) with the insertion end 226 (FIG. 6A) initially being placed through the insert opening 62 and directed toward the trailing end seal 54. Insertion of the base portion 220 continues until the tab 228 is guided through the gap 60. The liner 36 (FIG. 2A) is then removed as described above, with the adhesive coating (not shown) effectively laminating the base portion 220 within the pocket 20. As shown, while at least a section of the base portion 220 is now permanently fixed to and within the pocket 20, at least a section of the label portion 222 extends outwardly beyond the pocket 20. Thus, a caregiver or other user can easily interact with the label portion 222 as desired. For example, the label portion 222 can be detached from the base portion 220 (via the tear line 224) and/or the label 230 can be removed from the label portion 222 and applied to a separate structure.

Figure 7:
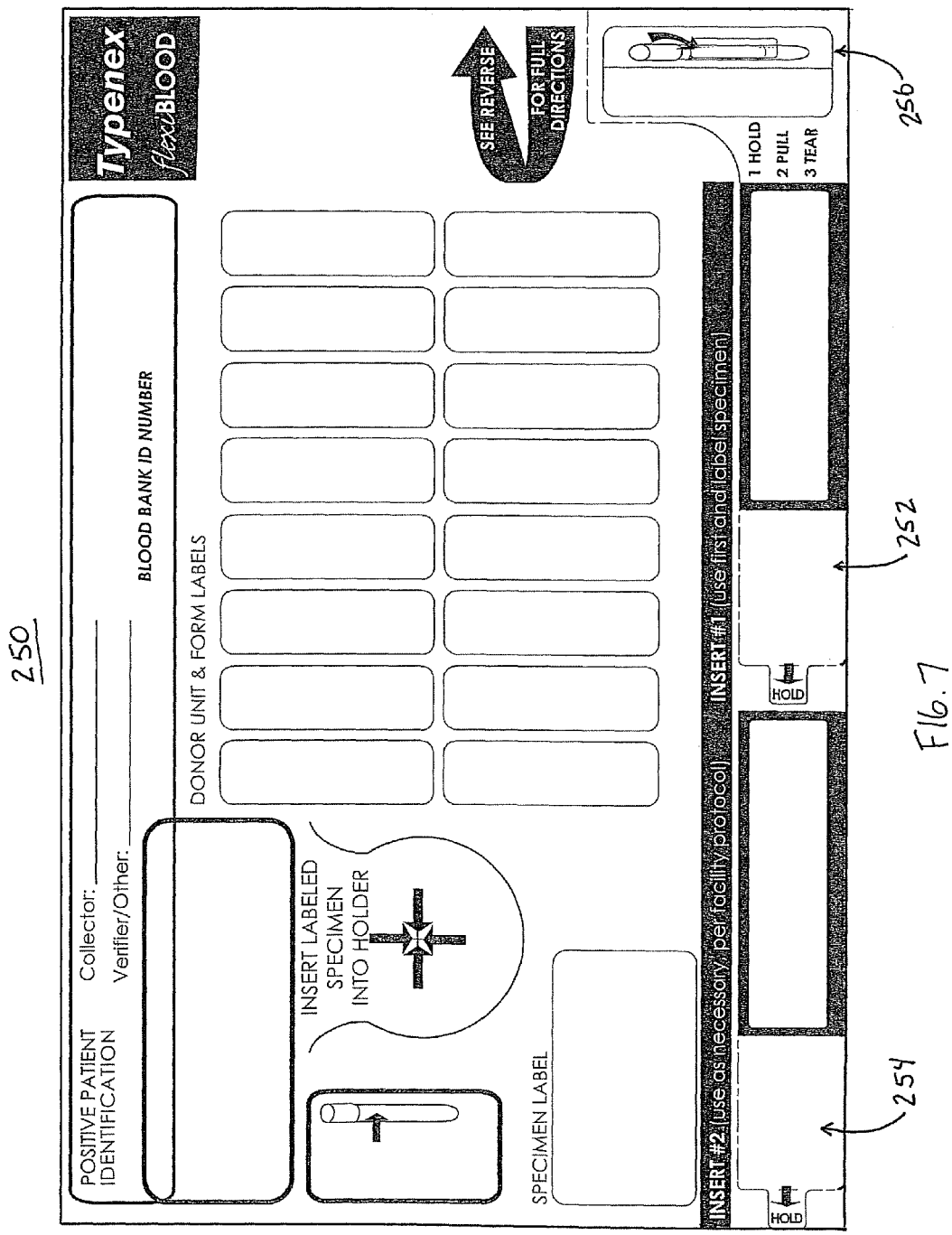
FIG. 7 is a simplified top plan view of another form incorporating an insert in accordance with principles of the present disclosure and useful with the recipient verification system of FIG. 1.

The insert 200 described above can assume a variety of other formats. In this regard, FIG. 7 illustrates another embodiment of a form 250 carrying two inserts 252, 254 useful with the recipient verification bands of the present disclosure. The inserts 252, 254 are highly akin to the insert 200 described above (except that the second insert 254 does not include a label portion 256), are readily detachable from a remainder of the form 250, and can be assembled to the band 12 (FIG. 1) as described above.

While some embodiments of the band 12 (FIG. 2A) have been described as incorporating complete side seams to effectuate formation of the corresponding pocket 20 (FIG. 2), other constructions are also envisioned. For example, a portion of another band 300 useful as part of a recipient identification system in accordance with the present disclosure is shown in FIG. 8A and includes a pocket 302 coupled to a strap 304. The pocket 302 is generally defined by opposing, first and second pocket layers 306, 308. Opposing side seals 310, 312 bond opposing side edges of the first pocket layer 306 to the second pocket layer 308, thereby defining an interior pocket region (hidden in FIG. 8A). The side seals 310, 312 terminate at a point longitudinally spaced from a leading end 314 of the first pocket layer 306. With this construction, the un-bonded region of the first pocket layer 306 forms a flap 316 that is freely movable relative to the second pocket layer 308 in the assembly arrangement shown (i.e., prior to insertion of an insert). The second pocket layer 308 carries a secondary adhesive coating 318 opposite the flap 316. A removable liner (not shown) is initially provided over the secondary adhesive coating 318.

With the above construction, the positive identification state facilitated by the band 300 includes inserting the insert (not shown) within the pocket 302 as described above. In connection with this insertion, the liner (not shown) over the secondary adhesive coating 318 is intact. Once desired insertion and placement of the insert is achieved, the insert is laminated to the pocket 302 as described above, for example by activating a primary adhesive coating 320 (e.g., removing a liner). The secondary adhesive coating 318 is then also exposed or activated (e.g., the liner removed), and the insert and the flap 316 caused to press against, and thus bond to, the secondary adhesive coating 318. As a result, the flap 316 is more completely bonded or sealed to the second pocket layer 308 and over the insert. Thus, any opening to the interior pocket region (hidden) at an access opening that might otherwise exist at the leading end 314 of the first pocket layer 306 is substantially sealed (e.g., a water tight-like seal).

FIG. 8B illustrates a portion of a related embodiment band 350 including a pocket 352 coupled to a strap 354. The pocket 352 is defined by opposing, first and second pocket layers 356, 358, and side seals 360, 362. The side seals 360, 362 terminate at a location spaced from a leading end 364 of the first pocket layer 356, which is otherwise not initially bonded to the second pocket layer 358, to define a flap 366. During use, in the positive identification state, a secondary adhesive 368 carried along the flap 366 is activated (e.g., a temporary release liner (not shown) initially covering the adhesive 368 is removed), with the first pocket layer 356 then being bonded to the second pocket layer 358 so as to establish a water tight-like seal at the leading end 364.

With any of the above-described recipient verification systems, color coding is sometimes used in tandem with identification verification systems. For example, some hospitals associate certain colors with patients from certain wards within the hospital (e.g. emergency room, pediatrics, etc.) and subsequently utilize patient identification means with the ability to display said colors. In accordance with this premise, the identification verification systems described in the present disclosure may also provide a means to display a variety of different colors. More specifically, the colors may be obtained by coloring any component of the aforementioned recipient verification systems or inserts. For example and with reference to FIG. 1, in some embodiments in accordance with principles of the present disclosure, different components of the band 12 (e.g. the strap 22, closure mechanism 16, pocket 20, etc.) may be partially or completely colored. In an alternative embodiment, the insert 14 attached to the band 12 may be likewise partially or completely colored appropriately (e.g. via specific font colors, or whole insert colors).

Although the present disclosure has been described with reference to preferred embodiments, workers skilled in the art will recognize that changes can be made in form and detail without departing from the spirit and scope of the present disclosure.

What is claimed is:

1. A recipient verification system comprising:
a band having a pocket coupled to a strap, the pocket being transitionable from an open arrangement to a closed arrangement and including:
a first layer defining a leading end, a trailing end, and opposing first and second side edges,
a second layer opposite the first layer,
a first side seal between the second layer and the first side edge of the first layer,
a second side seal between the second layer and the second side edge of the first layer,
wherein the first and second layers combine to form an interior pocket region between the first and second side seals,
an end seal between the second layer and at least a portion of the first layer adjacent the trailing end, wherein a length of the interior pocket region is defined as a distance between the end seal and the leading end,
an adhesive coating along at least a portion of an inner face of at least one of the first and second layers, wherein a length of the adhesive coating is less than the length of the interior pocket region,
a removable liner disposed over the adhesive coating,
wherein the open arrangement includes the liner disposed over the adhesive coating, an opening to the interior pocket region being defined by the first layer opposite the trailing end, and a portion of the removable liner projects outwardly from the interior pocket region via the opening,
wherein the closed arrangement includes the liner removed from the adhesive coating.

2. The recipient verification system of claim 1, further comprising:
an insert formed separate from the band and configured to display recipient information;
wherein the system is configured to provide an assembly state in which the insert is insertable into the interior pocket region with the pocket in the open arrangement, and a positive identification state in which the insert is permanently affixed to the pocket upon transitioning of the pocket to the closed arrangement.

3. The recipient verification system of claim 2, wherein:
a length of the interior pocket region is defined between the end seal and the leading end of the first layer; and
a width of the interior pocket region is defined between the first and second side seals;
and further wherein a width of the insert is slightly less than the width of the interior pocket region, and a length of the insert is greater than the length of the interior pocket region.

4. The recipient verification system of claim 3, wherein the insert include opposing, first and second ends, and further wherein the system is configured such that in the positive identification state, the first end of the insert abuts the end seal and the second end of the insert extends outwardly beyond the pocket opening.

5. The recipient verification system of claim 3, wherein the length and width of the insert correspond with the length and width of the interior pocket region such that in the assembly state, the opposing side seals and the end seal align the insert within the interior pocket region.

6. The recipient verification system of claim 3, wherein the positive identification state includes at least one of the first and second layers being bonded to the insert via the adhesive coating.

7. The recipient verification system of claim 6, wherein the adhesive coating is disposed on at least a portion of an inner face of each of the first and second layers, and further wherein the positive identification state includes the insert being laminated to both of the first and second layers.

8. The recipient verification system of claim 6, wherein the insert includes a base segment and a label segment, the label segment coupled to the base segment and carrying a removable label, and further wherein the positive identification state includes at least a portion of the base segment located within the interior pocket region and laminated to at least one of the first and second layers, and at least a portion of the label segment located outside of the interior pocket region.

9. The recipient verification system of claim 8, wherein the label segment is detachable from the base segment.

10. The recipient verification system of claim 8, wherein base segment includes an adhesive layer, and further wherein the positive identification state includes the adhesive layer of the base segment bonded to one of the first and second pocket layers and the adhesive coating of the pocket bonds the base segment to an other of the first and second pocket layers such that the insert is laminated to both of the first and second layers.

11. The recipient verification system of claim 1, wherein the end seal includes a first end seal section extending from the first side edge adjacent the trailing end, and a second end seal section extending from the second side edge adjacent the trailing end, and further wherein the first end section is discontinuous with the second end section.

12. The recipient verification system of claim 11, wherein a gap is formed between the first and second end seal sections, and further wherein the open arrangement includes a length of the leading end being free of bonding to the second layer, and even further wherein a length of the gap is less than the length of the portion of the leading end otherwise free of bonding to the second layer.

13. The recipient verification system of claim 11, further comprising an insert defining an insertion end and an exposed end, the insertion end forming a tab, and further wherein the system is configured such that in an assembly state, the insertion end is initially inserted through the opening and into the interior pocket region, and then from the interior pocket region and through the gap.

14. The recipient verification system of claim 11, wherein the pocket further comprises a primary end seal located between the end seal and the trailing end, the primary end seal extending continuously between the first and second side seals.

15. The recipient verification system of claim 1, wherein the end seal extends continuously between and interconnects the side seals adjacent the trailing end.

16. The recipient verification system of claim 1, further comprising a printable form, wherein the printable form includes a detachable insert configured for assembly to the band.

17. The recipient verification system of claim 16, wherein the form additionally includes a plurality of removable labels.

18. The recipient verification system of claim 17, wherein the form includes a recipient identification code displayed on the insert and each of the plurality of removable labels.

19. The recipient verification system of claim 18, wherein the recipient verification code includes a printed bar code.

20. The recipient verification system of claim 1, wherein the first side seal extends along, and encompasses an entirety of, the first side edge, and the second side seal extends along an encompasses an entirety of the second side edge.

21. The recipient verification system of claim 1, wherein the first and second side seals each terminate at point longitudinally spaced from the leading end such that in the open arrangement, the first layer defines a flap terminating at the leading end, the flap being movable relative to the second layer.

22. The recipient verification system of claim 1, wherein the adhesive coating encompasses a majority of the inner face of the at least one of the first and second layers.

23. A method of manufacturing a recipient verification system, the method comprising:
  forming a band comprising a pocket coupled to a strap, the pocket being transitionable from an open arrangement to a closed arrangement and including:
    forming a first layer defining a leading end, a trailing end, and opposing first and second side edges,
    forming a second layer opposite the first layer,
    disposing an adhesive coating along at least a portion of an inner face of at least one of the first and second layers,
    disposing a removable liner over the adhesive coating,
    forming a permanent first side seal between the second layer and the first side edge of the first layer,
    forming a permanent second side seal between the second layer and the second side edge of the first layer,
    wherein the first and second layers combine to form an interior pocket region between the first and second side seals,
    forming a permanent end seal between the second layer and at least a portion of the first layer adjacent the trailing end, the permanent end seal being spaced from the adhesive coating,
    wherein the open arrangement includes the liner disposed over the adhesive coating, the first layer sealed to the second layer at each of the side seals and the end seal, and an opening to the interior pocket region is defined by the first layer,
    wherein the closed arrangement includes the liner removed from the adhesive coating.

24. The method of claim 23, further comprising:
  forming an insert separate from the band and configured to display recipient information;
  wherein the system is configured to provide an assembly state in which the insert is insertable into the interior pocket region with the pocket in the open arrangement, and a positive identification state in which the insert is permanently affixed to the pocket upon transitioning of the pocket to the closed arrangement.

25. The method of claim 24, wherein forming an insert includes:
  creating a printed form on label stock material; and
  forming partial cuts in the form to define the insert such that the insert is detachable from the form.

26. The method of claim 25, wherein creating a printed form includes:
   forming a plurality of removable labels in the label stock material;
   applying a unique identification code to each of the removable labels, the insert, and at least one other location on the form apart from the removable labels and the insert.

27. A method of using a recipient verification system, the method comprising:
   receiving a band including a pocket coupled to a strap, the pocket forming an interior pocket region defined by opposing, first and second layers, wherein the first layer is bonded to the second layer along opposing side seals and an at least partial end seal, and further wherein an opening to the interior pocket region is defined opposite the end seal, the band further including an adhesive coating within the interior pocket region and carried by at least one of the first and second layers, the adhesive coating provided apart from the opposing side seals and the end seal;
   receiving an insert formed apart from the band, the insert extending between opposing, first and second terminal ends, wherein the insert displays an identification code;
   sliding the first terminal end into the interior pocket region via the opening until the first terminal end is beyond the adhesive coating and within the interior pocket region;
   laminating the insert to the pocket via the adhesive coating; and
   securing the band to a wearer's appendage.

28. The method of claim 27, wherein following the step of laminating the insert to the pocket, a first portion of the insert is disposed within the interior pocket region and a second portion of the insert extends outside of the interior pocket region.

29. The method of claim 28, wherein the second portion includes a removable label.

30. The method of claim 28, wherein the second portion is detachable from the first portion.

31. The method of claim 27, wherein laminating the insert to the pocket includes removing a liner covering the adhesive coating.

32. The method of claim 27, wherein the insert is provided as part of a form, the method further comprising:
   entering recipient information on to a face of the form; and
   detaching the insert from the form.

33. The method of claim 27, wherein the step of sliding the first terminal end into the interior pocket region includes sliding the first terminal end within the interior pocket region until the first terminal end contacts the end seal.

34. The method of claim 33, further comprising holding the first terminal end at the end seal during the step of laminating the insert to the pocket.

35. The system of claim 1, wherein the end seal is spaced from the adhesive coating in a direction of a length of the interior pocket region.

* * * * *